US00PP14845P2

(12) United States Plant Patent
Wilfret

(10) Patent No.: US PP14,845 P2
(45) Date of Patent: Jun. 1, 2004

(54) CALADIUM PLANT NAMED 'FLORIDA WHITEWATER'

(50) Latin Name: *Caladium×hortulanum*
Varietal Denomination: Florida Whitewater

(75) Inventor: Gary J. Wilfret, Sarasota, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 10/408,145

(22) Filed: Apr. 6, 2003

(51) Int. Cl.[7] ..... A01H 5/00
(52) U.S. Cl. ..... Plt./373
(58) Field of Search ..... Plt./373

*Primary Examiner*—Bruce R. Campell
*Assistant Examiner*—Annette H Para
(74) *Attorney, Agent, or Firm*—C. A. Whealy

(57) ABSTRACT

A distinct cultivar of Caladium plant named 'Florida Whitewater', characterized by its compact and densely-foliated plant habit suitable for container production; outwardly arching and symmetrical plant form; and white and dark green bi-colored leaves that are lanceolate in shape.

1 Drawing Sheet

Botanical classification/cultivar designation: *Caladium×hortulanum* cultivar Florida Whitewater.

BACKGROUND OF THE INVENTION

The present Invention relates to a new and distinct cultivar of Caladium plant, botanically known as *Caladium×hortulanum,* commercially referred to as a lance-leaf Caladium, and hereinafter referred to by the cultivar name Florida Whitewater.

The new cultivar is a product of a planned and controlled breeding program conducted by the Inventor in Bradenton, Fla. The objective of the breeding program is to create densely-foliated compact Caladium cultivars with uniquely variegated foliage.

The new cultivar originated from a cross-pollination made in 1985 of the *Caladium×hortulanum* cultivar White Wing, not patented, as the female, or seed, parent, with the *Caladium×hortulanum* cultivar White Queen, not patented, as the male, or pollen, parent. The cultivar Florida Whitewater was discovered and selected in 1986 as a plant within the progeny of the stated cross-pollination in a controlled environment in Bradenton, Fla.

Asexual propagation of the new cultivar by tuber divisions in Bradenton, Fla., has shown that the unique features of this new Caladium plant are stable and reproduced true to type in successive generations of asexual propagation.

SUMMARY OF THE INVENTION

The new Caladium has not been observed under all possible environmental conditions. The phenotype may vary somewhat with variations in environment such as temperature and light intensity, without, however, any variance in genotype.

The following traits have been repeatedly observed and are determined to be the unique characteristics of 'Florida Whitewater'. These characteristics in combination distinguish 'Florida Whitewater' as a new and distinct cultivar:

1. Compact and densely-foliated plant habit suitable for container production.
2. Outwardly arching and symmetrical plant form.

3. White and dark green bi-colored leaves that are lanceolate in shape.

Plants of the new Caladium can be compared to plants of the female parent, the cultivar White Wing. When grown in side-side comparisons in Bradenton, Fla., plants of the new Caladium differed from plants of the cultivar White Wing, in the following characteristics:

1. Plants of the new Caladium were more compact than plants of the cultivar White Wing.
2. Plants of the new Caladium had more leaves per plant than plants of the cultivar White Wing.
3. Plants of the new Caladium had narrower leaves than plants of the cultivar White Wing.

Plants of the new Caladium can be compared to plants of the male parent, the cultivar White Queen. When grown in side-side comparisons in Bradenton, Fla., plants of the new Caladium differed from plants of the cultivar White Queen in the following characteristics:

1. Plants of the new Caladium had lanceolate-shaped leaves whereas plants of the cultivar White Wing had cordate-shaped leaves.
2. Leaves of plants of the new Caladium had white-colored venation whereas leaves of plants of the cultivar White Wing had red-colored venation.

Plants of the new Caladium are similar in leaf coloration to the cultivar Jackie Suthers, not patented. However, when grown in side-side comparisons in Bradenton, Fla., plants of the new Caladium differed from plants of the cultivar Jackie Suthers, in the following characteristics:

1. Plants of the new Caladium were more compact than plants of the cultivar Jackie Suthers.
2. Plants of the new Caladium had more leaves per plant than the cultivar Jackie Suthers.
3. Plants of the new Caladium had narrower leaves than plants of the cultivar Jackie Suthers.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Caladium. The photograph is a side perspective view of a typical plant of 'Florida Whitewater' grown in a container.

DETAILED BOTANICAL DESCRIPTION

The aforementioned photograph, following observations, measurements and comparisons describe 14-week old plants (from planting a tuber division) grown in Bradenton, Fla. during the spring in a shaded glass-covered greenhouse and under commercial production conditions in 15-cm containers. During the production of the plants, day temperatures were about 32° C., night temperatures were about 21° C. and light levels were about 2,000 to 3,000 foot-candles.

In the following description, color references are made to The Royal Horticultural Society Colour Chart, 1995 Edition, except where general terms of ordinary dictionary significance are used.

Botanical classification: *Caladium×hortulanum* cultivar Florida Whitewater.

Parentage:

*Female, or seed, parent.*—*Caladium×hortulanum* cultivar White Wing, not patented.

*Male, or pollen, parent.*—*Caladium×hortulanum* cultivar White Queen, not patented.

Propagation:

*Type.*—By tuber divisions.

*Tuber description.*—Number of dominant buds per tuber: About 10 to 12. Diameter: About 6.4 to 8.9 cm. Color: Epidermis, 200C; interior, 8B.

*Time to initiate roots on a tuber division.*—About 9 days at 27° C.

*Time to produce a fully rooted tuber division.*—About 37 days at 27° C.

*Root description.*—Dense, thick and white in color.

Plant description:

*Plant habit.*—Compact and densely-foliated, suitable for 10 to 15-cm containers.

*Plant form.*—Outwardly arching and symmetrical plant habit.

*Growth habit.*—Somewhat erect when leaves are developing, becoming outwardly arching as leaves develop.

*Plant height.*—About 25 cm from soil level to top of leaf plane.

*Plant spread.*—About 30 cm.

*Foliage description.*—Quantity: About 73 per plant. Length: About 19 cm. Width: About 9 cm. Shape: Lanceolate. Apex: Acuminate. Base: Attenuate. Margin: Entire; undulate. Aspect: Initially upright, then outwardly arching. Texture, upper and lower surfaces: Smooth, glabrous, durable and flexible. Venation pattern: Penniform. Color: Upper surface: Margins, 137A, about 5 mm in width; irregular mottling paralleling the margins, 157A; central interveinal area, 155C; venation, 139C. Lower surface: Margins, 191B; central interveinal area, 155C; venation, 191B. Petiole: Aspect: Erect to arching. Length: About 25 cm. Diameter: About 2 to 5 mm. Strength: Strong. Color: 199B; densely covered with brown, 200B, speckles.

*Flower description.*—Flower development has not been observed on plants of the new Caladium.

Disease/pest resistance: Plants of the new Caladium have not been observed to be resistant to pathogens or pests common to Caladium.

Temperature/weather tolerance: Plants of the new Caladium have been observed to be tolerant to temperatures as low as 10° C. and as high as 38° C. Plants of the new Caladium have been observed to be tolerant to rain and wind. Plants of the new Caladium will tolerate full sun conditions in Florida without leaf scorching.

It is claimed:

1. A new and distinct cultivar of Caladium plant named 'Florida Whitewater', as illustrated and described.

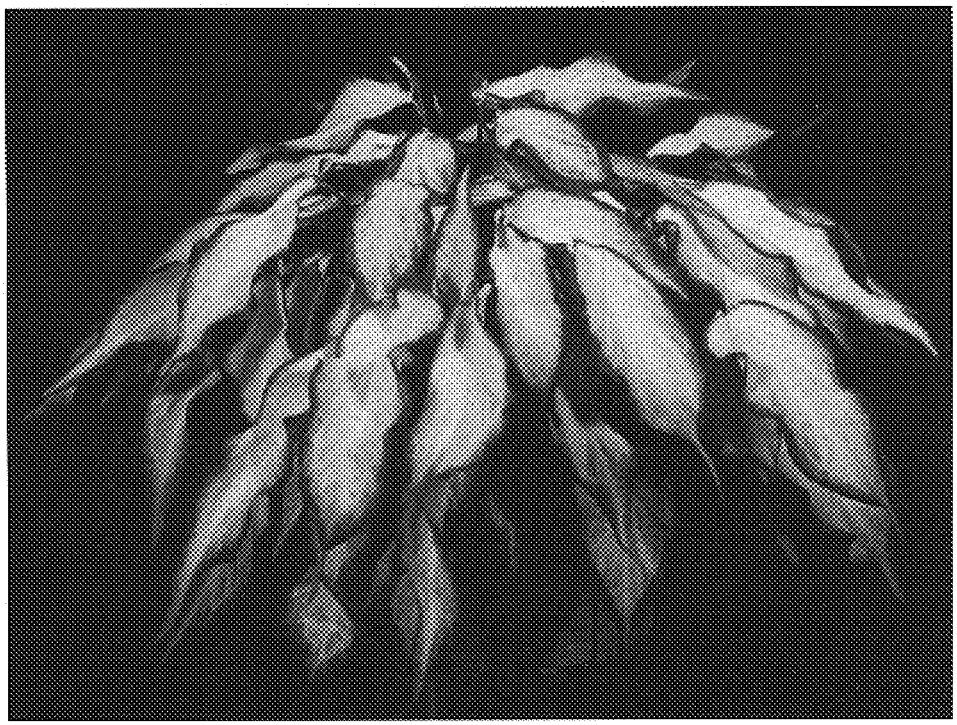

* * * * *